US005750736A

United States Patent [19]

Sisti

[11] Patent Number: 5,750,736
[45] Date of Patent: May 12, 1998

[54] METHOD FOR ACYLATING 10-DEACETYLBACCATIN III SELECTIVELY AT THE C-10 POSITION

[75] Inventor: Nicholas J. Sisti, Jeffersonville, Pa.

[73] Assignee: NaPro BioTherapeutics, Inc., Boulder, Colo.

[21] Appl. No.: 678,759

[22] Filed: Jul. 11, 1996

[51] Int. Cl.$^6$ ............................................. C07D 305/14
[52] U.S. Cl. ........................................ 549/510; 549/511
[58] Field of Search ................................ 549/510, 511

[56] References Cited

U.S. PATENT DOCUMENTS 5,229,526  7/1993  Holton ................................ 549/213

OTHER PUBLICATIONS

Chemical Studies of 10-Deacetyl Baccatin III. Hemisynthesis of Taxol Derivatives:, F. Gueritte-Voegelein et al, *Tetrahedron*, vol. 42, No. 16, pp. 4451 to 4460, 1986.

"Modified Taxols. 3. Preparation and Acylatioin of Baccatin III" Magri et al, *J. Org. Chem.*, 1986, 51, 3239–3242.

"A Highly Efficient, Practical Approach to Natural Taxol", Denis et al, *J. Am. Chem. Co.*, vol. 110, No. 2, 1988.

"The Chemistry of TAxol", Kinston, *Pharma. Ther.*, vol. 52, pp.1-34, 1991.

"A Chemoselective Approach to Functionalize the C–10 Position of 10–Deacetylbaccatin III. Synthesis and Biological Properties of Novel C–10 Taxol Analogues", Kant et al., *Tetrahedron Letters*, vol. 35, No. 31, pp. 5543–5546, 1994.

*Primary Examiner*—Ba K. Trinh
*Attorney, Agent, or Firm*—Timothy J. Martin; Michael R. Henson

[57] ABSTRACT

A method of acylating 10-deacetylbaccatin III at the C-10 position over the C-7 hydroxy position thereof to produce baccatin III is accomplished first by dissolving 10-deacetylbaccatin III in an anhydrous ether solvent, such as tetrahydrofuran, at a reduced temperature, preferably −78° C. At least an equivalent of a lithium base, preferably about two equivalents n-butyl lithium, is next added followed by the addition of an acylating agent, such as acetyl chloride. The resulting solution is quenched, for example with ammonium chloride, to eliminate excess of the lithium base and the acylating agent. The result is baccatin III in solution. The baccatin III may be recovered by removing the ether solvent under vacuum to produce a residue that may then be dissolved, for example in ethyl acetate, with this solution being washed to remove unwanted salt compounds. Recrystallization and column chromatography may be employed to purify the baccatin III.

24 Claims, No Drawings

METHOD FOR ACYLATING 10-DEACETYLBACCATIN III SELECTIVELY AT THE C-10 POSITION

FIELD OF THE INVENTION

The present invention broadly concerns taxane chemistry. Broadly, the present invention is directed to the direct acylation of 10-deacetylbaccatin III at the C-10 position over the C-7 position. The present invention especially concerns the acylation of 10-deacetylbaccatin III to provide baccatin III.

BACKGROUND OF THE INVENTION

Taxane compounds have received increasing attention among the scientific and medical community because of indications that various ones of these compounds, including paclitaxel (referred to in the literature as "taxol"), docetaxel (TAXOTERE®) and others, exhibit anti-tumor activity.

Paclitaxel is a naturally occurring taxane diterpenoid which is found in several species of the Yew (genus taxus, Family Taxaceae). Unfortunately, the concentration of this compound is very low. While the presence of this compound is found in the yew tree at extremely low concentrations, there are many other taxane compounds, especially 10-deacetylbaccatin III, which are able to be extracted in relatively high concentrations from renewable portions of the yew. 10-deacetylbaccatin III has the general formula:

In an effort to increase the available supply of the anti-tumor compounds, efforts have been made to partially synthesize the paclitaxel, docetaxel and other analogs by joining a chiral, non-racemic side chain and a protected baccatin III backbone. In some instances, it is preferable to start with baccatin III as the backbone unit while in other instances, it is possible to use 10-deacetylbaccatin III as the starting backbone unit. Baccatin III, which has the formula as follows:

is differentiated from 10-deacetylbaccatin III by the presence of the acetate group at the C-10 location.

There have been efforts reported in the past to acylate 10-deacetylbaccatin III to provide baccatin III, but these efforts have met with mixed results. It may be observed that the 10-deacetylbaccatin III molecule has four hydroxy positions, at C-1, C-7, C-10 and C-13. A first impression from a review of this molecule would suggest that the hydroxyl positions would all be statistically acylated by an acylating compound. However, this is not true due to the steric environment of the C-1 and C-13 sites. Indeed, the hydroxy group at C-1 is so sterically encumbered that essentially no acylation would ordinarily occur at this position. Moreover, the hydroxy group at C-13 is the next most encumbered position, and it is difficult to acylate at the C-13 site. Indeed, it is for this reason that the esterification of a protected baccatin III backbone with the phenylisoserine side chain, for example, has proved difficult because the C-13 hydroxy group is located within the concave region of the hemispherical taxane skeleton, thus making it difficult to access. Accordingly, attempts to acylate 10-deacetylbaccatin III results in little acylation at the C-13 position.

Reactions at the C-7 and C-10 hydroxy positions on the 10-deacetylbaccatin III molecule, are quite different as these sites are dramatically more reactive than those at C-1 and C-13. Of the two sites, it has been observed that the C-7 site is more reactive. As Denis et al. "A Highly Efficient, Practical Approach to Natural Taxol", *Journal of the American Chemical Society*, 5917, reports the results of attempted acylation of the 10-deacetylbaccatin III molecule using pyridine with a large excess of an acylating agent such as acetyl chloride. As reported in this journal article, acylation was most favored at the C-7. Acylation at C-7, of course, is highly undesirable because once acylated, it has not been demonstrated that the acetyl group at C-7 can be selectively removed thus making the compound undesirable as a precursor to any known antineoplastic taxane. Moreover, any selective acylation at C-10 is in extremely small quantities so as to produce a small yield.

As a result of the reactivity of the C-7 hydroxy position, attempts at converting 10-deacetylbaccatin III to baccatin III have been directed to a first step of selectively protecting the 10-deacetylbaccatin III molecule at the C-7 hydroxy position, for example, with a triethylsilyl (TES) group. This technique is reported in the Denis et al article, cited above.

Here, 10-deacetylbaccatin III is converted to C-7 TES-protected 10-deacetylbaccatin III followed by the acylation of the compound at the C-10 location. Here, 10-deacetylbaccatin III is reacted with a large excess of TES-Cl and pyridine.

Alternatively, C-7 TES-protected baccatin III may be produced according to a procedure described in Kant et al "A Chemo-Selective Approach To Functionalize The C-10 Position of 10-deacetylbaccatin III Syntheses and Biological Properties of Novel C-10 Taxol® Analogs", *TETRAHEDRON LETTERS*, Volume 35, No. 31, TP 5543–5546 (1994). In this article, 10-deacetylbaccatin III is mixed with dimethylformamide (DMF) under a nitrogen atmosphere, and imidazole is added while stirring. TES-Cl is added dropwise followed by a quenching of the mixture. After obtaining the C-7 TES protected 10-deacetylbaccatin III, it is then acylated at C-10 using n-butyl lithium or lithium hexamethyl disilizane and acetyl chloride. The resulting C-7 TES-protected baccatin III is then deprotected at the C-7 position by any convenient method. An example of such a method uses aqueous hydrochloric acid. However, in the semi-syntheses of paclitaxel deprotection usually is performed only after attaching the phenylisoserine side chain so that 10-deacetylbaccatin III is not converted directly into baccatin III.

SUMMARY OF THE INVENTION

It is an object of the present invention to provide a new and useful method for the conversion of 10-deacetylbaccatin III into the baccatin III molecule.

3

Another object of the present invention is to provide a simple chemical route from 10-deacetylbaccatin III to baccatin III which avoids the necessity of protecting the C-7 hydroxy position of 10-deacetylbaccatin III and the deprotection thereof following the step of acylating at the C-10 position.

A further object of the present invention is to provide an efficient method for producing high yields of baccatin III from 10-deacetylbaccatin III.

Still a further object of the present invention is to provide a relatively inexpensive process for the production of baccatin III from the more abundant 10-deacetylbaccatin III which may be used in commercial processes, including the semi-syntheses of paclitaxel and its analogs.

According to the present invention, then, a method is described for producing baccatin III from 10-deacetylbaccatin III. This method comprises a first step of dissolving a selected quantity of 10-deacetylbaccatin III in an acceptable ether solvent therefor to form a first solution at a first temperature. Next, at least one equivalent, but preferably 1.25 equivalents, of n-butyl lithium is mixed into the first solution to form a second solution. An equivalent of an acylating agent is then added to the second solution at a second temperature to form a third solution. Finally, the third solution is quenched with a suitable quenching compound that is effective to eliminate any of the excess n-butyl lithium and excess of the acylating agent from the third solution in order to produce the fourth solution containing baccatin III.

According to the preferred method, the ether solvent is selected from a group consisting of tetrahydrofuran and polyethers, and this ether solvent in any event, may be anhydrous. Likewise, the acylating agent is preferably selected from a group consisting of acetyl chloride and acetic anhydride with a preferred acelating agent being acetyl chloride. The quenching compound is preferred to be ammonium chloride.

It is preferred that the reaction take place at a reduced temperature. Here, the 10-deacetylbaccatin III is dissolved in the solvent at a temperature of −20° C. or less, but preferably about −78° C. The n-butyl lithium is then mixed into the first solution at this temperature and the acylating agent is added at a second temperature which is preferred to be −20° C. or less, but again most preferably at about −78° C. The third solution is then warmed to about 0°C. over a period of about one hour after quenching. Further, it is desired that the various solutions be stirred during the various processing steps. Here, the second solution may be stirred for about five minutes before adding the preferred acetyl chloride and the third solution is stirred for about thirty minutes before quenching.

In any event, it is desirable to further process the fourth solution to purify the resulting baccatin III. Here, the ether solvent is removed under vacuum after the quenching step thereby to reduce the fourth solution to a first residue. The first residue may then be dissolved in ethyl acetate to produce a fifth solution followed by the washing of the fifth solution to remove unwanted salt compounds. This step of washing is preferably with water and brine. The fifth solution is then reduced to a second residue and the second residue is purified. The step of purification may be accomplished either by recrystallization or column chromatography.

These and other objects of the present invention will become more readily appreciated and understood when the following detailed description of the exemplary embodiment is considered.

DETAILED DESCRIPTION OF THE EXEMPLARY EMBODIMENT

The present invention broadly concerns the conversion of 10-deacetylbaccatin III into baccatin III without the need to protect the reported more reactive C-7 position of the 10-deacetylbaccatin III molecule. The present method has been found to surprisingly produce high yields of baccatin III directly from 10-deacetylbaccatin III with the yields typically being on the order of 70% baccatin III.

This result is unexpected due to the general belief that the C-7 hydroxy position is more highly reactive and thus selectively acylates in preference to the C-10 hydroxy site. However, the present process indicates that selective acylation at the C-10 hydroxy position of the 10-deacetylbaccatin III molecule can occur without significant amounts of the detrimental acylation at the C-7 position when the reaction takes place in the presence of a lithium base to form a lithium anion at C-10.

The reaction according to the present invention may be diagrammed as follows:

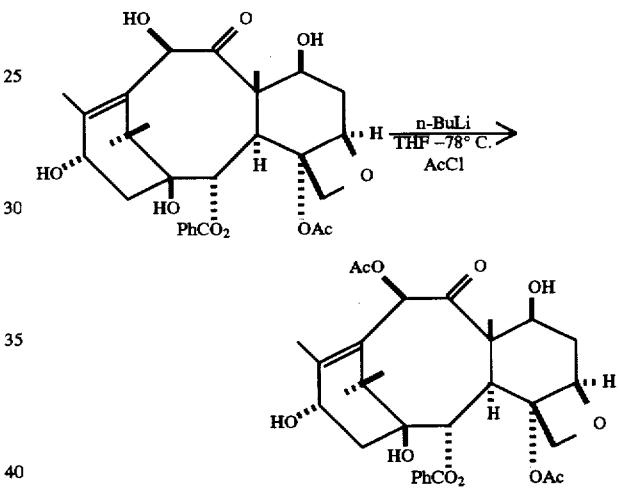

Here, a selected quantity of 10-deacetylbaccatin III is dissolved in an acceptable ether solvent to form a first solution at a first temperature. The preferable ether solvent is tetrahydrofuran (THF). This step is conducted under a nitrogen atmosphere, and it is important that the solvent be anhydrous since the presence of water or humidity can impede or destroy the ability for the reaction to proceed. The step of dissolving the 10-deacetylbaccatin III is preferably at temperature of −20° C. or less although it is preferred that the first solution be at a temperature of about −78° C.

Next, n-butyl lithium (1.6 m in hexane) is added to the first solution over a period of approximately one minute and the resulting second solution is stirred for about five minutes at the reduced temperature. It is preferable that about approximately 1.25 equivalents of n-butyl lithium although at least one equivalent of n-butyl lithium is added to the first solution with an acceptable of range of being 1-2 equivalents of the n-butyl lithium. Excess n-butyl lithium beyond this range would increase the amount of C-7, C-10 di-acylated baccatin III.

After stirring the second solution for about five minutes, an acylating agent is added at a second reduced temperature, again −20° C. or less, but preferably −78° C. The preferred acylating agent is acetyl chloride, and one equivalent of acetyl chloride is added to the second solution to form a third solution that is stirred for an additional thirty minutes at the reduced temperature. After stirring, the third solution is quenched with a suitable quenching compound that is effective to eliminate excess n-butyl lithium and excess quantities of the acylating agent therefrom to produce a fourth solution containing the baccatin III. The preferred quenching compound is ammonium chloride.

After adding the ammonium chloride, the mixture is slowly warmed to about 0° C. over an interval of about one hour. After reaching this temperature, the solvents are removed under vacuum to reduce the fourth solution to a first residue.

The first residue may be further concentrated and purified. This is preferably accomplished by dissolving the first residue in ethyl acetate to form a fifth solution that is then washed with water and brine to remove unwanted salt compounds from the fifth solution. The fifth solution is then reduced under vacuum to produce a second residue. Purification of the second residue may then be accomplished as is known in the art. Here, the residue may be column chromatographed to get substantially pure baccatin III. Alternatively, the second residue may be recrystallized, for example, in ethyl acetate:hexane to result in the target baccatin III compound.

Yields from this process indicate that approximately 70% of the 10-deacetylbaccatin III is converted to baccatin III with about 20% of the 10-deacetylbaccatin III remaining unreacted. Traces of C-7, C-10 di-acetate baccatin III are present due to the dual acylation at the C-7 and C-10 hydroxy positions. However, no significant amounts of the C-7 acetate of 10-deacetylbaccatin III were noted. The selected acylation at the C-10 position suggests that the reaction proceeds through the C-10 lithium alkoxide of 10-deacetylbaccatin III intermediate. this intermediate has the formula:

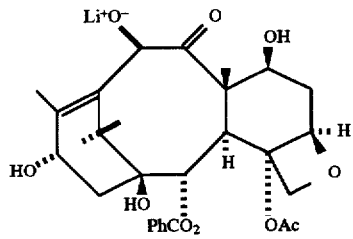

While it is preferred that tetrahydrofuran be the solvent into which the 10-deacetylbaccatin III is first dissolved, other ether solvents, including polyethers may be acceptable. While n-butyl lithium has been employed in the above-described reaction, it should be suitable to use other lithium bases, especially alkyl lithium bases in the reaction. Further, while the preferred acylating agent is acetyl chloride, it should be possible to use acetic anhydride or acetyl bromide or other suitable acylating agent although it would be expected that the reaction may proceed at different rates.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

I claim:

1. A method of acylating 10-deacetylbaccatin III at a C-10 position over a C-7 hydroxy position thereof, comprising the steps of:
   (a) dissolving a selected quantity of 10-deacetylbaccatin III in an acceptable ether solvent therefor to form a first solution at a first temperature;
   (b) mixing at least one equivalent of a lithium base into the first solution to form a second solution;
   (c) adding at least an equivalent of an acylating agent to the second solution at a second temperature to form a third solution; and
   (d) quenching the third solution with a suitable quenching compound that is effective to eliminate excess of the lithium base and said acylating agent therefrom to produce a fourth solution containing baccatin III.

2. A method according to claim 1 wherein said ether solvent is selected from a group consisting of: tetrahydrofuran and polyethers.

3. A method according to claim 1 wherein said ether solvent is anhydrous.

4. A method according to claim 1 wherein said acylating agent is selected from a group consisting of: acetyl chloride and acetic anhydride.

5. A method according to claim 1 wherein said quenching compound is ammonium chloride.

6. A method according to claim 1 wherein said first temperature is −20° C. or less.

7. A method according to claim 6 wherein said first temperature is about −78° C.

8. A method according to claim 7 wherein said second temperature is about −78° C.

9. A method according to claim 8 wherein the third solution is warmed to about 0° C. over a period of about one hour after quenching.

10. A method according to claim 1 wherein 1.0 to 2.0 equivalents of n-butyl lithium is mixed into the first solution.

11. A method according to claim 1 wherein about 1.25 equivalents of n-butyl lithium is mixed into the first solution.

12. A method according to claim 1 wherein said second solution is stirred for a first period of time at the first temperature before adding the acylating agent and wherein said third solution is stirred for a second period of time at the second temperature before quenching.

13. A method according to claim 1 including the step of removing the ether solvent under vacuum after the quenching step thereby to reduce the fourth solution to a first residue.

14. A method according to claim 13 including the step of dissolving the first residue in ethyl acetate to produce a fifth solution followed by washing to remove unwanted salt compounds and reducing the fifth solution to a second residue followed by purifying the second residue.

15. A method according to claim 14 wherein the step of purifying the second residue is accomplished by a purification step selected from a group consisting of: recrystallization and column chromatography.

16. A method according to claim 1 wherein the lithium base is an alkyl lithium base.

17. A method according to claim 16 wherein the alkyl lithium base is n-butyl lithium.

18. A method of producing baccatin III from 10-deacetylbaccatin II, comprising the steps of:
   (a) dissolving a selected quantity of 10-deacetylbaccatin III in an acceptable ether solvent therefor to form a first solution at a first temperature;

(b) mixing at least one equivalent of n-butyl lithium into the first solution to form a second solution;

(c) adding at least an equivalent of an acylating agent to the second solution at a second temperature to form a third solution; and (d) quenching the third solution with a suitable quenching compound that is effective to eliminate excess n-butyl lithium and said acylating agent therefrom to produce a fourth solution containing baccatin III.

19. A method of producing baccatin III from 10-deacetylbaccatin III, comprising the steps of:

(a) dissolving a selected quantity of 10-deacetylbaccatin III in anhydrous tetrahydrofuran to form a first solution at a first reduced temperature of −20° C. or less;

(b) mixing at least one equivalent of n-butyl lithium into the first solution to form a second solution;

(c) adding at least an equivalent of acetyl chloride to the second solution at a second reduced temperature of −20° C. or less to form a third solution; and (d) quenching the third solution with a quenching compound effective to eliminate excess quantities of n-butyl lithium and the acetyl chloride to produce a fourth solution containing baccatin III.

20. The method according to claim 19 wherein the first and second reduced temperatures are about −78° C.

21. The method according to claim 19 wherein the step of dissolving the 10-deacetylbaccatin III in anhydrous tetrahydrofuran is conducted under a nitrogen atmosphere.

22. The method according to claim 19 wherein the second solution is stirred for about five minutes before adding the acetyl chloride and the third solution is stirred about thirty minutes before quenching.

23. The method according to claim 19 including the steps of warming the fourth solution to a temperature of about 0° C., next removing solvents therefrom under vacuum to produce a first residue, dissolving the first residue in ethyl acetate from a fifth solution, washing the fifty solution with water and brine, reducing the fifth solution to a second residue followed by purifying the second residue to produce purified baccatin III.

24. An intermediate for the production of baccatin III having the formula:

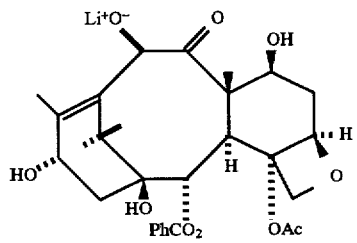

* * * * *